(12) United States Patent
Kuwabara

(10) Patent No.: US 10,512,440 B2
(45) Date of Patent: Dec. 24, 2019

(54) RADIOGRAPHY SYSTEM, IMAGE PROCESSING METHOD, AND IMAGE PROCESSING PROGRAM

(71) Applicant: FUJIFILM CORPORATION, Minato-ku, Tokyo (JP)

(72) Inventor: Takeshi Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 271 days.

(21) Appl. No.: 15/655,889

(22) Filed: Jul. 21, 2017

(65) Prior Publication Data

US 2018/0028139 A1 Feb. 1, 2018

(30) Foreign Application Priority Data

Jul. 29, 2016 (JP) ................................ 2016-150589

(51) Int. Cl.
*A61B 6/00* (2006.01)

(52) U.S. Cl.
CPC .......... *A61B 6/5252* (2013.01); *A61B 6/4266* (2013.01); *A61B 6/4291* (2013.01); *A61B 6/505* (2013.01)

(58) Field of Classification Search
CPC ... A61B 6/4291; A61B 6/4266; A61B 6/5252; A61B 6/461; A61B 6/4233; A61B 6/505
See application file for complete search history.

(56) References Cited

U.S. PATENT DOCUMENTS

2012/0155610 A1* 6/2012 Murakoshi ........... A61B 6/4291
378/62
2016/0035451 A1* 2/2016 Tsuji .................... A61B 6/4266
378/62

FOREIGN PATENT DOCUMENTS

WO 2013047193 A1 4/2013

* cited by examiner

*Primary Examiner* — David P Porta
*Assistant Examiner* — Fani Boosalis
(74) *Attorney, Agent, or Firm* — Solaris Intellectual Property Group, PLLC

(57) ABSTRACT

A radiography system includes: a radiography apparatus including a first radiation detector and a second radiation detector which is provided so on a side of the first radiation detector from which the radiation is transmitted and emitted, and a grid that is configured to remove scattered radiation included in the radiation transmitted through a subject; and an acquisition unit that is configured to acquire, using the grid, a first radiographic image captured by the first radiation detector and a second radiographic image captured by the second radiation detector; and a removal unit that is configured to detect and remove a first grid image, which is an image of the grid, from the first radiographic image acquired by the acquisition unit, and to remove the image of the grid from the second radiographic image acquired by the acquisition unit, using the first grid image.

15 Claims, 8 Drawing Sheets

RADIOGRAPHY SYSTEM, IMAGE PROCESSING METHOD, AND IMAGE PROCESSING PROGRAM

CROSS-REFERENCE TO RELATED APPLICATION

This application claims priority from Japanese Patent Application No. 2016-150589, filed on Jul. 29, 2016, the disclosure of which is incorporated by reference herein in its entirety.

BACKGROUND

Field of the Invention

The present disclosure relates to a radiography system, an image processing method, and an image processing program.

Related Art

For example, as disclosed in WO2013/047193A, a radiography apparatus has been known that comprises two radiation detectors each of which includes a plurality of pixels that accumulate a larger amount of charge as they are irradiated with a larger amount of radiation and which are provided so as to be stacked.

For example, as disclosed in WO2013/047193A, a technique has been known which includes a grid that removes scattered radiation generated by the transmission of radiation through a subject from the radiation transmitted through the subject.

In general, as in the technique disclosed in WO2013/047193A, in a case in which a grid is provided and a radiographic image is captured, the captured radiographic image includes the shade of the grid as the image of stripes. Therefore, in the related art, in general, image processing for removing a grid image from a captured radiographic image is performed.

However, in a case in which radiographic images are captured by two radiation detectors disclosed in, for example, WO2013/047193A, radiation that has been transmitted through the radiation detector provided on the incident side of the radiation reaches the radiation detector provided on the emission side of the radiation. Therefore, the amount of radiation that reaches the radiation detector provided on the emission side of the radiation is less than the amount of radiation that reaches the radiation detector provided on the incident side and the amount of radiation used to generate a radiographic image is reduced.

Therefore, in some cases, it is difficult to appropriately extract grid information for removing a grid image from the radiographic image captured by the radiation detector that is provided on the emission side of the radiation and image processing for removing the grid image from the radiographic image is not appropriately performed.

SUMMARY

The present disclosure has been made in view of the above-mentioned problems and an object of the present disclosure is to provide a technique that can perform appropriate image processing for an acquired radiographic image even when the amount of radiation emitted to a second radiation detector is less than the amount of radiation emitted to a first radiation detector.

In order to achieve the object, according to an aspect of the present disclosure, there is provided a radiography system comprising: a radiography apparatus comprising a first radiation detector in which a plurality of pixels, each of which includes a conversion element that generates a larger amount of charge as it is irradiated with a larger amount of radiation, are two-dimensionally arranged, a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, and a grid that removes scattered radiation included in the radiation transmitted through a subject; an acquisition unit that is configured to acquire, using the grid, a first radiographic image captured by the first radiation detector and a second radiographic image captured by the second radiation detector; and a removal unit that is configured to detect and remove a first grid image, which is an image of the grid, from the first radiographic image acquired by the acquisition unit and removes the image of the grid from the second radiographic image acquired by the acquisition unit, using the first grid image.

In the radiography system according to the above-mentioned aspect of the present disclosure, the removal unit may be configured to generate, using the first grid image, a pseudo second grid image, which is a pseudo image of the image of the grid included in the second radiographic image, from the first grid image, and to remove the generated pseudo second grid image as the image of the grid from the second radiographic image.

In the radiography system according to the above-mentioned aspect of the present disclosure, the removal unit may be configured to generate the pseudo second grid image from the first grid image, using an amount of deviation between the first radiation detector and the second radiation detector in a direction intersecting a stacking direction of the first radiation detector and the second radiation detector and an enlargement ratio of the second radiographic image to the first radiographic image.

In the radiography system according to the above-mentioned aspect of the present disclosure, the removal unit may be configured to derive a rotation angle of the second radiation detector with respect to the first radiation detector as the amount of deviation in the direction intersecting the stacking direction. The removal unit may be configured to generate the pseudo second grid image from the first grid image, using the rotation angle, the enlargement ratio, and folding back at a Nyquist frequency that is defined by a gap between adjacent pixels among the plurality of pixels of the first radiation detector.

In the radiography system according to the above-mentioned aspect of the present disclosure, the removal unit may be configured to, in a case in which a second grid image, which is an image of the grid, is capable of being detected from the second radiographic image and a difference in information of the grid between the second grid image and the pseudo second grid image is in a predetermined range, remove the second grid image as the image of the grid from the second radiographic image, without using the first grid image.

The difference that is used in the radiography system according to the above-mentioned aspect of the present disclosure may be at least one of a difference between the number of grids in the second grid image and the number of grids in the pseudo second grid image, or a relative angle of the grid between the second grid image and the pseudo second grid image.

In the radiography system according to the above-mentioned aspect of the present disclosure, each of the first radiation detector and the second radiation detector may include a light emitting layer that emits light as a result of being irradiated with radiation, the plural pixels of each of the first radiation detector and the second radiation detector may generate and accumulate the charge as a result of receiving the light, and the light emitting layer of the first radiation detector and the light emitting layer of the second radiation detector may have different compositions.

In the radiography system according to the above-mentioned aspect of the present disclosure, the light emitting layer of the first radiation detector may include CsI and the light emitting layer of the second radiation detector may include GOS.

The radiography system according to the above-mentioned aspect of the present disclosure may further comprise a derivation unit that is configured to derive at least one of bone mineral content or bone density, using the first radiographic image and the second radiographic image from which the image of the grid has been removed by the removal unit.

In the radiography system according to the above-mentioned aspect of the present disclosure present, the radiography apparatus may further comprise a radiation limitation member that is provided between the first radiation detector and the second radiation detector and absorbs a larger amount of specific component than other components in energy forming the radiation.

In order to achieve the object, according to another aspect of the present disclosure, there is provided an image processing method using a radiography apparatus including a first radiation detector in which plural pixels, each of which includes a conversion element that generates a larger amount of charge as it is irradiated with a larger amount of radiation, are two-dimensionally arranged, a second radiation detector which is provided so as to be stacked on a side of the first radiation detector from which the radiation is transmitted and emitted and in which plural pixels, each of which includes a conversion element that generates a larger amount of charge as it is irradiated with a larger amount of radiation, are two-dimensionally arranged, and a grid that is configured to remove scattered radiation included in the radiation transmitted through a subject, the method including: acquiring a first radiographic image captured by a first radiation detector and a second radiographic image captured by the second radiation detector, using the grid; detecting and removing a first grid image, which is an image of the grid, from the first radiographic image; and removing a second grid image, which is the image of the grid, from the second radiographic image, using the first grid image.

In order to achieve the object, according to still another aspect of the present disclosure, there is provided a non-transitory storage medium storing an image processing program that causes a computer to perform an image processing using a radiography apparatus including a first radiation detector in which plural pixels, each of which includes a conversion element that generates a larger amount of charge as it is irradiated with a larger amount of radiation, are two-dimensionally arranged, a second radiation detector which is provided so as to be stacked on a side of the first radiation detector from which the radiation is transmitted and emitted and in which plural pixels, each of which includes a conversion element that generates a larger amount of charge as it is irradiated with a larger amount of radiation, are two-dimensionally arranged, and a grid that is configured to remove scattered radiation included in the radiation transmitted through a subject, the image processing including: acquiring a first radiographic image captured by a first radiation detector and a second radiographic image captured by the second radiation detector, using the grid; detecting and removing a first grid image, which is an image of the grid, from the first radiographic image; and removing a second grid image which is the image of the grid from the second radiographic image, using the first grid image.

According to the present disclosure, appropriate image processing can be performed for an acquired radiographic image even when the amount of radiation emitted to a second radiation detector is less than the amount of radiation emitted to a first radiation detector.

DETAILED DESCRIPTION

Hereinafter, an embodiment of the invention will be described in detail with reference to the drawings.

Figure 1:
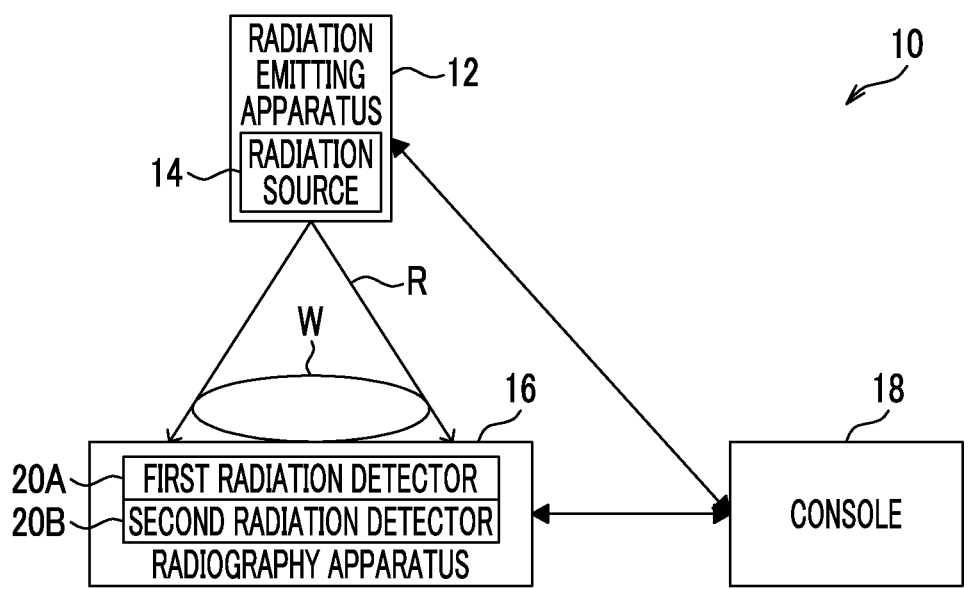
FIG. 1 is a block diagram illustrating an example of the structure of a radiography system according to an embodiment.

First, the structure of a radiography system 10 according to this embodiment will be described with reference to FIG. 1. As illustrated in FIG. 1, the radiography system 10 comprises a radiation emitting apparatus 12, a radiography apparatus 16, and a console 18. The console 18 according to this embodiment is an example of an image processing apparatus according to the invention.

The radiation emitting apparatus 12 according to this embodiment comprises a radiation source 14 that irradiates a subject W, which is an example of an imaging target, with radiation R such as X-rays. An example of the radiation emitting apparatus 12 is a treatment cart. A method for instructing the radiation emitting apparatus 12 to emit the radiation R is not particularly limited. For example, in a case in which the radiation emitting apparatus 12 comprises an irradiation button, a user, such as a doctor or a radiology technician, may press the irradiation button to instruct the emission of the radiation R such that the radiation R is emitted from the radiation emitting apparatus 12. In addition, for example, the user may operate the console 18 to instruct the emission of the radiation R such that the radiation R is emitted from the radiation emitting apparatus 12.

When receiving a command to start the emission of the radiation R, the radiation emitting apparatus 12 emits the radiation R from the radiation source 14 according to emission conditions, such as a tube voltage, a tube current, and an irradiation period.

The radiography apparatus 16 according to this embodiment comprises a first radiation detector 20A and a second radiation detector 20B that detect the radiation R which has been emitted from the radiation emitting apparatus 12 and then transmitted through the subject W. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

Figure 2:
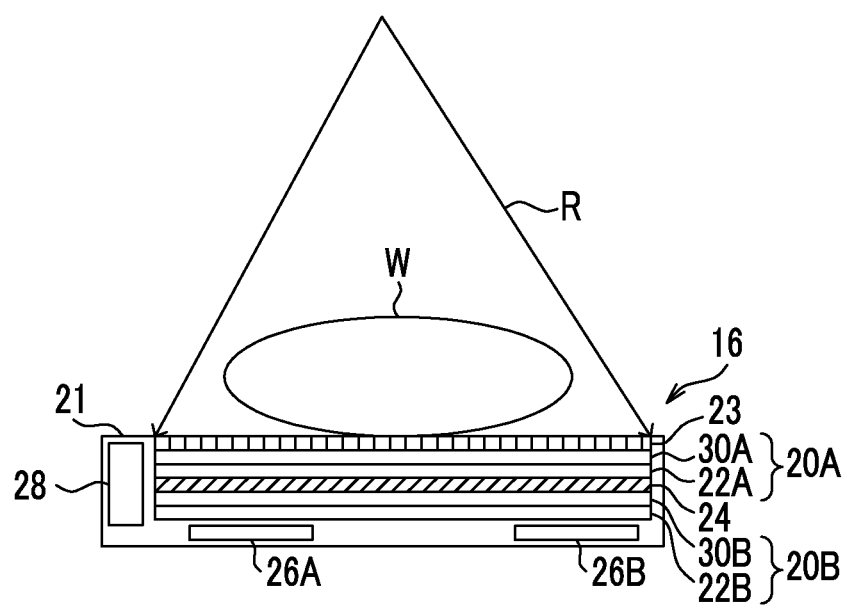
FIG. 2 is a side cross-sectional view illustrating an example of the structure of a radiography apparatus according to this embodiment.

Next, the structure of the radiography apparatus 16 according to this embodiment will be described with reference to FIG. 2. As illustrated in FIG. 2, the radiography apparatus 16 comprises a plate-shaped housing 21 that transmits the radiation R and has a waterproof, antibacterial, and airtight structure. The housing 21 includes the first radiation detector 20A, the second radiation detector 20B, a grid 23, a radiation limitation member 24, a control board 26A, a control board 26B, and a case 28.

The first radiation detector 20A is provided on the incident side of the radiation R and the second radiation detector 20B is provided so as to be stacked on the side of the first radiation detector 20A from which the radiation R is transmitted and emitted in the radiography apparatus 16. The first radiation detector 20A comprises a thin film transistor (TFT) substrate 30A and a scintillator 22A which is an example of a light emitting layer that is irradiated with the radiation R and emits light corresponding to the amount of radiation R emitted. The TFT substrate 30A and the scintillator 22A are stacked in the order of the TFT substrate 30A and the scintillator 22A from the incident side of the radiation R. The term "stacked" means a state in which the first radiation detector 20A and the second radiation detector 20B overlap each other in a case in which the first radiation detector 20A and the second radiation detector 20B are seen from the incident side or the emission side of the radiation R in the radiography apparatus 16 and it does not matter how they overlap each other. For example, the first radiation detector 20A and the second radiation detector 20B, or the first radiation detector 20A, the radiation limitation member 24, and the second radiation detector 20B may overlap while coming into contact with each other or may overlap with a gap therebetween in the stacking direction.

The second radiation detector 20B comprises a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the side of the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the scintillator 22A includes CsI (Tl) (cesium iodide having thallium added thereto) as a main component and the scintillator 22B includes gadolinium oxysulfide (GOS) as a main component. GOS has a higher sensitivity to the high-energy radiation R than CsI. In addition, a combination of the composition of the scintillator 22A and the composition of the scintillator 22B is not limited to the above-mentioned example and may be a combination of other compositions or a combination of the same compositions.

The grid 23 that removes scattered radiation generated by the transmission of the radiation R through the subject W from the radiation R transmitted through the subject W is provided on the incident side of the radiation R in the first radiation detector 20A. The removal of the scattered radiation from the radiation R makes it possible to obtain, for example, the effect of preventing a reduction in the contrast of the radiographic image and to improve the quality of the radiographic image.

The radiation limitation member 24 that limits the transmission of the radiation R is provided between the first radiation detector 20A and the second radiation detector 20B. An example of the radiation limitation member 24 is a metal plate made of, for example, copper or tin. It is preferable that a variation in the thickness of the radiation limitation member 24 is equal to or less than 1% in the incident direction of the radiation R in order to uniformize limitations (transmissivity) on the radiation.

The control board 26A is provided so as to correspond to the first radiation detector 20A and electronic circuits, such as an image memory 56A and a control unit 58A which will be described below, are formed on the control board 26A. The control board 26B is provided so as to correspond to the second radiation detector 20B and electronic circuits, such as an image memory 56B and a control unit 58B which will be described below, are formed on the control board 26B. The control board 26A and the control board 26B are provided on the side of the second radiation detector 20B which is opposite to the incident side of the radiation R.

As illustrated in FIG. 2, the case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the structure of a main portion of an electric system of the radiography apparatus 16 according to this embodiment will be described with reference to FIG. 3.

Figure 3:
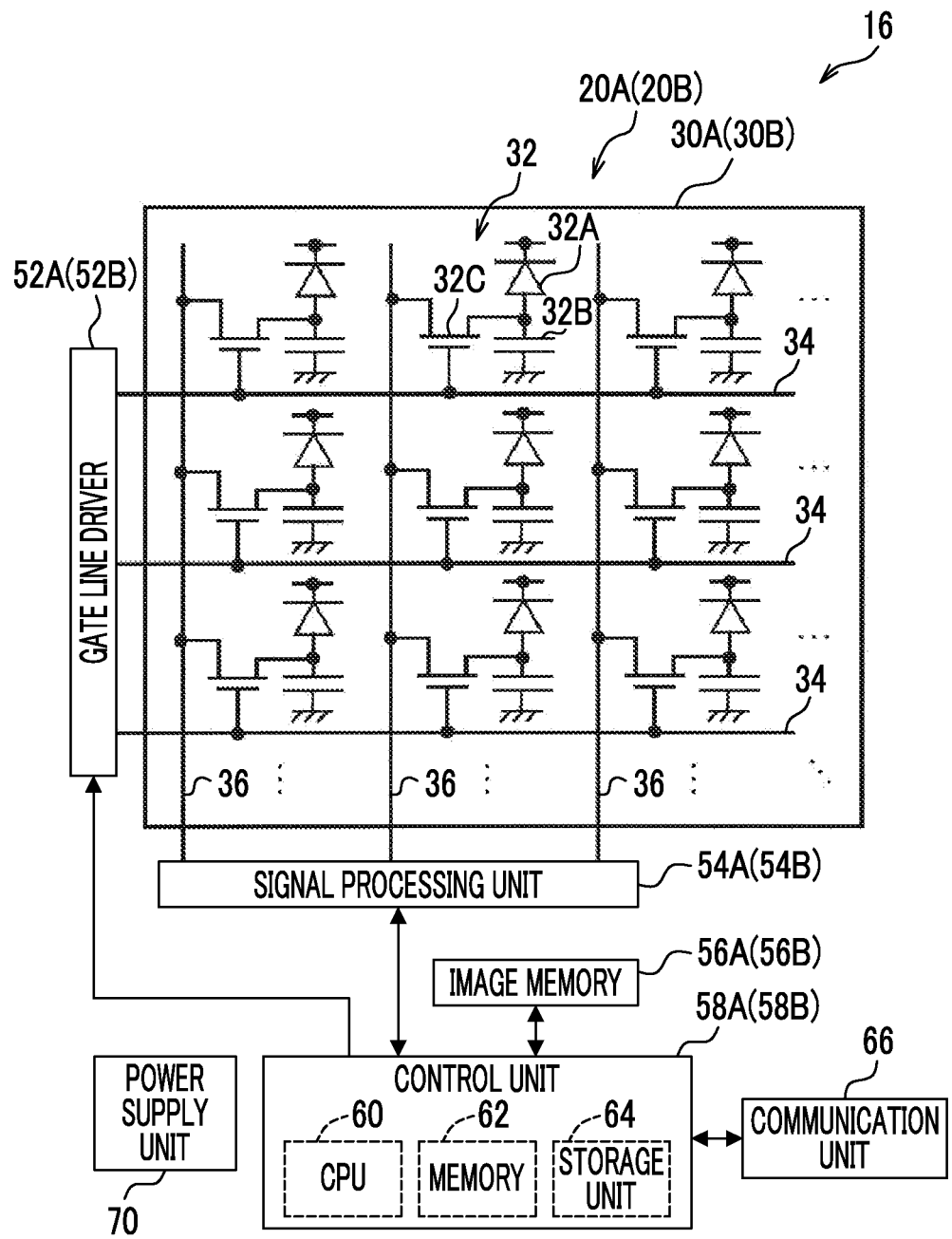
FIG. 3 is a block diagram illustrating an example of the structure of a main portion of an electric system of the radiography apparatus according to this embodiment.

As illustrated in FIG. 3, a plurality of pixels 32 are two-dimensionally provided in one direction (a row direction in FIG. 3) and an intersection direction (a column direction in FIG. 3) that intersects the one direction on the TFT substrate 30A. The pixel 32 includes a sensor unit 32A, a capacitor 32B, and a field effect thin film transistor (TFT; hereinafter, simply referred to as a "thin film transistor") 32C. The sensor unit 32A according to this embodiment is an example of a conversion element according to the invention.

The sensor unit 32A includes, for example, an upper electrode, a lower electrode, and a photoelectric conversion film which are not illustrated, absorbs the light emitted from the scintillator 22A, and generates charge. The capacitor 32B accumulates the charge generated by the sensor unit 32A. The thin film transistor 32C reads the charge accumulated in the capacitor 32B and outputs the charge in response to a control signal. The charge, of which the amount increases as the amount of radiation emitted increases, is accumulated in the pixel 32 according to this embodiment by the above-mentioned structure.

A plurality of gate lines 34 which extend in the one direction and are used to turn on and off each thin film transistor 32C are provided on the TFT substrate 30A. In addition, a plurality of data lines 36 which extend in the intersection direction and to which the charge read by the thin film transistors 32C in an on state is output are provided on the TFT substrate 30A.

A gate line driver 52A is provided on one side of two adjacent sides of the TFT substrate 30A and a signal processing unit 54A is provided on the other side. Each gate line 34 of the TFT substrate 30A is connected to the gate line driver 52A and each data line 36 of the TFT substrate 30A is connected to the signal processing unit 54A.

The thin film transistors 32C corresponding to each gate line 34 on the TFT substrate 30A are sequentially turned on (in units of row illustrated in FIG. 3 in this embodiment) by control signals which are supplied from the gate line driver 52A through the gate lines 34. The charge which is read by the thin film transistor 32C in an on state is transmitted as an electric signal through the data line 36 and is input to the signal processing unit 54A. In this way, charge is sequentially read from each gate line 34 (in units of row illustrated in FIG. 3 in this embodiment) and image data indicating a two-dimensional radiographic image is acquired.

The signal processing unit 54A comprises amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer (not illustrated) and an analog/digital (A/D) converter (not illustrated) are connected to the output side of the sample-and-hold circuit in this order. The electric signals held by each sample-and-hold circuit are sequentially (serially) input to the multiplexer and are sequentially selected by the multiplexer. Then, the A/D converter converts the selected electric signals into digital image data.

The image memory 56A is connected to the signal processing unit 54A through the control unit 58A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A. In addition, the image memory 56A is connected to the control unit 58A.

The control unit 58A comprises a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same structures as the corresponding components of the first radiation detector 20A and thus the description thereof will not be repeated here. The control unit 58A and the control unit 58B are connected such that they can communicate with each other.

According to the above-mentioned structure, the radiography apparatus 16 according to this embodiment captures radiographic images using the first radiation detector 20A and the second radiation detector 20B.

Figure 4:
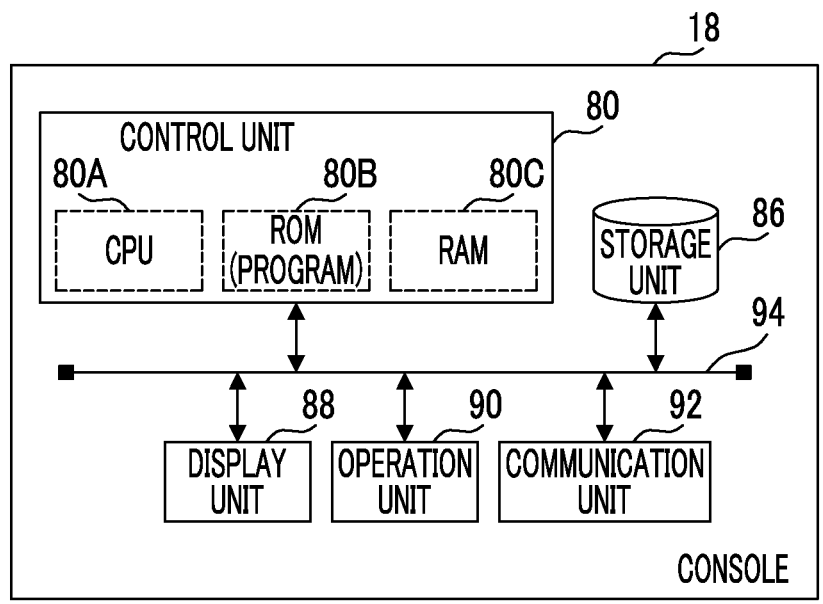
FIG. 4 is a block diagram illustrating an example of the structure of a main portion of an electric system of a console according to this embodiment.

Next, the structure of the console 18 according to this embodiment will be described with reference to FIG. 4. As illustrated in FIG. 4, the console 18 comprises a control unit 80. The control unit 80 comprises a CPU 80A that controls the overall operation of the console 18, a ROM 80B in which, for example, various programs or various parameters are stored in advance, and a RAM 80C that is used as, for example, a work area when the CPU 80A executes various programs.

In addition, the console 18 comprises a non-volatile storage unit 86 such as a hard disk drive (HDD). The storage unit 86 stores and holds image data indicating a radiographic image captured by the first radiation detector 20A, image data indicating a radiographic image captured by the second radiation detector 20B, and various other data. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data". In a case in which the "first radiographic image" and the "second radiographic image" are generically named, they are simply referred to as "radiographic images".

The console 18 further comprises a display unit 88, an operation unit 90, and a communication unit 92. The display unit 88 displays, for example, information related to imaging and a captured radiographic image. The user uses the operation unit 90 to input, for example, a command to capture a radiographic image and a command related to image processing for a captured radiographic image. For example, the operation unit 90 may have the form of a keyboard or may have the form of a touch panel that is integrated with the display unit 88. The communication unit 92 transmits and receives various kinds of information to and from the radiation emitting apparatus 12 and the radiography apparatus 16, using at least one of wireless communication or wired communication. In addition, the communication unit 92 transmits and receives various kinds of information to and from external systems, such as a picture archiving and communication system (PACS) and a radiology information system (RIS), using at least one of wireless communication or wired communication.

The control unit 80, the storage unit 86, the display unit 88, the operation unit 90, and the communication unit 92 are connected to each other through a bus 94.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A. In addition, the radiation limitation member 24 generally has the characteristic that it absorbs a larger number of low-energy components than high-energy components in energy forming the radiation R, which depends on the material forming the radiation limitation member 24. Therefore, the energy distribution of the radiation R that reaches the second radiation detector 20B has a larger number of high-energy components than the energy distribution of the radiation R that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has passed through the first radiation detector 20A and reached the radiation limitation member 24 is absorbed by the radiation limitation member 24. About 50% of the radiation R that has passed through the first radiation detector 20A and the radiation limitation member 24 and reached the second radiation detector 20B is absorbed by the second radiation detector 20B and is used to capture a radiographic image.

That is, the amount of radiation (the amount of charge generated by the second radiation detector 20B) used to capture a radiographic image by the second radiation detector 20B is about 20% of the amount of radiation used to capture a radiographic image by the first radiation detector 20A. In addition, the ratio of the amount of radiation used to capture a radiographic image by the second radiation detector 20B to the amount of radiation used to capture a radiographic image by the first radiation detector 20A is not limited to the above-mentioned ratio. However, it is preferable that the amount of radiation used to capture a radiographic image by the second radiation detector 20B is equal to or greater than 10% of the amount of radiation used to capture a radiographic image by the first radiation detector 20A in terms of diagnosis.

Figure 5:
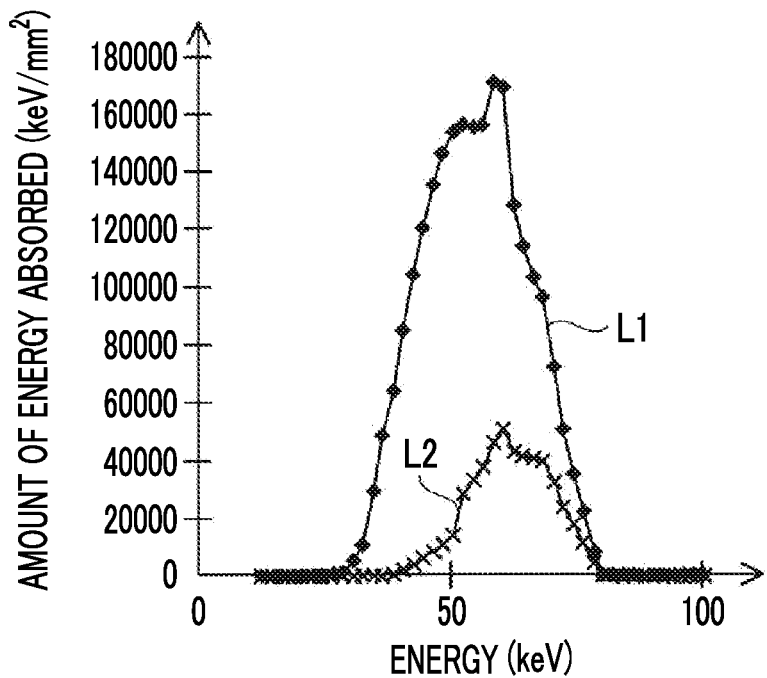
FIG. 5 is a graph illustrating the amount of radiation that reaches each of a first radiation detector and a second radiation detector according to this embodiment.

The radiation R is absorbed from a low-energy component. Therefore, for example, as illustrated in FIG. 5, the energy components of the radiation R that reaches the second radiation detector 20B do not include the low-energy components of the energy components of the radiation R that reaches the first radiation detector 20A. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In FIG. 5, a solid line L2 indicates the relationship between the energy of the radiation R absorbed by the second radiation detector 20B and the amount of radiation R absorbed per unit area.

Figure 6:
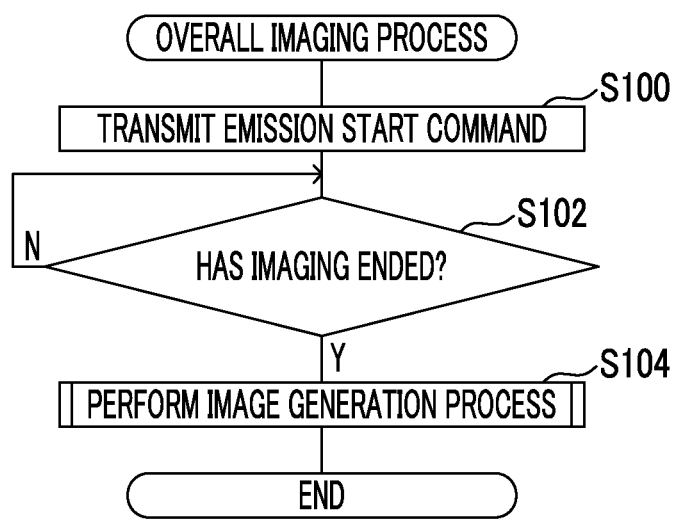
FIG. 6 is a flowchart illustrating an example of the flow of an overall imaging process according to this embodiment.

Next, the operation of the radiography system 10 according to this embodiment will be described. FIG. 6 is a flowchart illustrating an example of the flow of an overall imaging process performed by the control unit 80 of the console 18. Specifically, the CPU 80A of the control unit 80 executes an overall imaging processing program to perform the overall imaging process illustrated in FIG. 6. The overall imaging processing program is an example of an image processing program according to the invention. When the CPU 80A executes the overall imaging processing program, the control unit 80 functions as an example of an acquisition unit and a removal unit according to the invention.

In this embodiment, the overall imaging process illustrated in FIG. 6 is performed in a case in which the control unit 80 of the console 18 acquires an imaging menu including, for example, the name of the subject W, an imaging part, and the emission conditions of the radiation R from the user through the operation unit 90. The control unit 80 may acquire the imaging menu from an external system, such as an RIS, or may acquire the imaging menu input by the user through the operation unit 90.

In Step S100 of FIG. 6, the control unit 80 of the console 18 transmits information included in the imaging menu to the radiography apparatus 16 through the communication unit 92 and transmits the emission conditions of the radiation R to the radiation emitting apparatus 12 through the communication unit 92. Then, the control unit 80 transmits a command to start the emission of the radiation R to the radiography apparatus 16 and the radiation emitting apparatus 12 through the communication unit 92. When receiving the emission conditions and the emission start command transmitted from the console 18, the radiation emitting apparatus 12 starts the emission of the radiation R according to the received emission conditions. The radiation emitting apparatus 12 may comprise an irradiation button. In this case, the radiation emitting apparatus 12 receives the emission conditions and the emission start command transmitted from the console 18 and starts the emission of the radiation R according to the received emission conditions in a case in which the irradiation button is pressed.

In the radiography apparatus 16, the first radiation detector 20A captures the first radiographic image and the second radiation detector 20B captures the second radiographic image, on the basis of the information in the imaging menu transmitted from the console 18. In the radiography apparatus 16, the control units 58A and 58B perform various correction processes, such as offset correction and gain correction, for first radiographic image data indicating the captured first radiographic image and second radiographic image data indicating the captured second radiographic image, respectively, and store the corrected radiographic image data in the storage unit 64.

Then, in Step S102, the control unit 80 determines whether the capture of the radiographic images by the radiography apparatus 16 has ended. A method for determining whether the capture of the radiographic images has ended is not particularly limited. For example, each of the control units 58A and 58B of the radiography apparatus 16 transmits end information indicating that imaging has ended to the console 18 through the communication unit 66. In a case in which the end information is received, the control unit 80 of the console 18 determines that the capture of the radiographic images by the radiography apparatus 16 has ended.

For example, each of the control units 58A and 58B transmits the first radiographic image data and the second radiographic image data to the console 18 through the communication unit 66 after imaging ends. In a case in which the first radiographic image data and the second radiographic image data are received, the control unit 80 determines that the capture of the radiographic images by the radiography apparatus 16 has ended. In addition, in a case in which the first radiographic image data and the second radiographic image data are received, the console 18 stores the received first radiographic image data and the received second radiographic image data in the storage unit 86.

In a case in which the capture of the radiographic images by the radiography apparatus 16 has not ended, the determination result is "No" and the control unit 80 waits until the capture of the radiographic images by the radiography apparatus 16 ends. On the other hand, in a case in which the capture of the radiographic images by the radiography apparatus 16 has ended, the determination result is "Yes" and the control unit 80 proceeds to Step S104.

Figure 7:
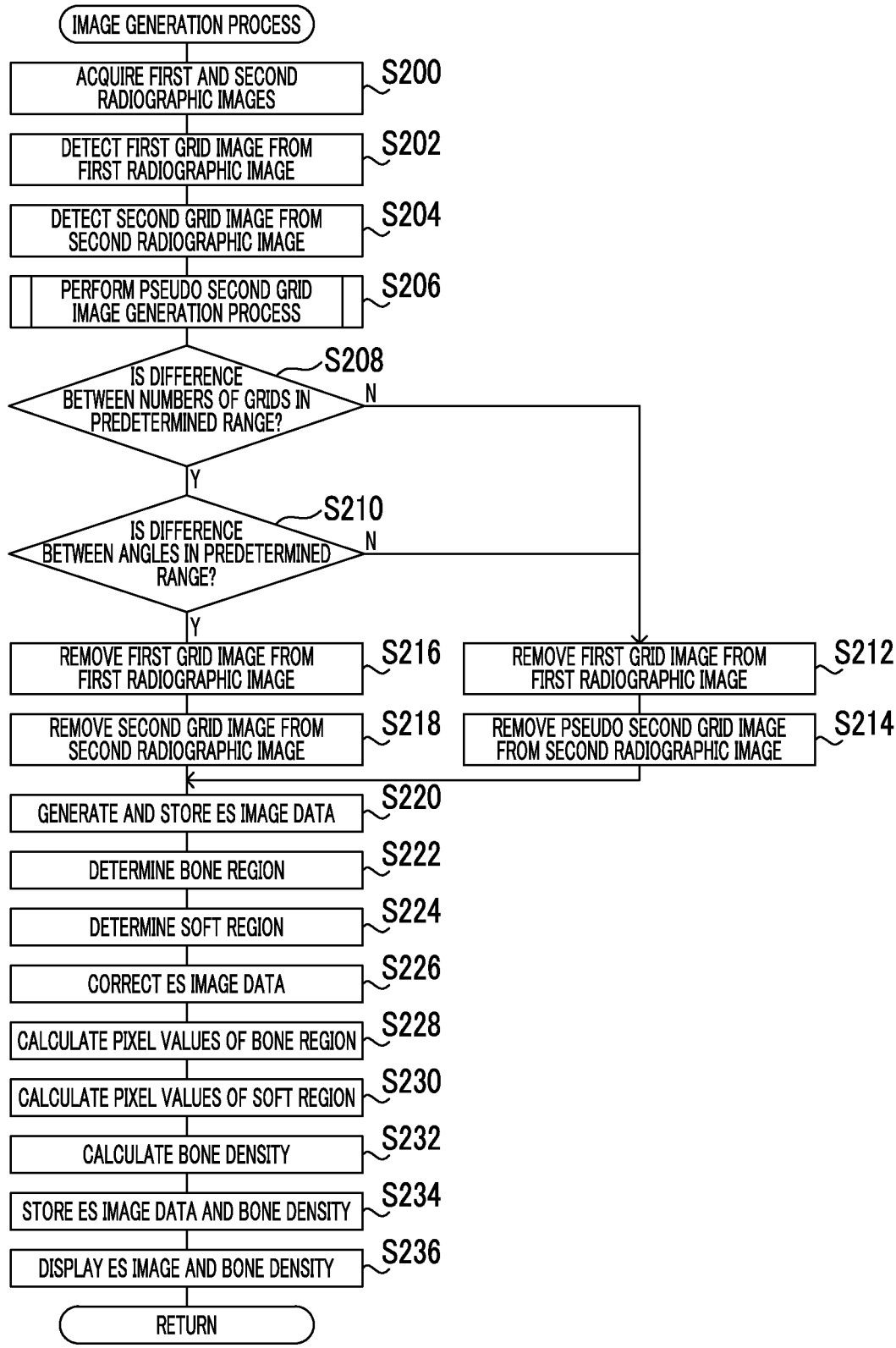
FIG. 7 is a flowchart illustrating an example of the flow of an image generation process in the overall imaging process according to this embodiment.

In Step S104, the control unit 80 performs an image generation process illustrated in FIG. 7 and ends the overall imaging process.

Next, the image generation process performed in Step S104 of the overall imaging process (see FIG. 6) will be described with reference to FIG. 7.

In the radiography apparatus 16 according to this embodiment, the radiation R transmitted through the grid 23 is emitted to the first radiation detector 20A and the second radiation detector 20B. Therefore, the grid 23 is included as a stripe image in the radiographic images captured by the first radiation detector 20A and the second radiation detector 20B. For this reason, in the image generation process illustrated in FIG. 7, image processing for removing the image of the grid 23 in each of the first radiographic image and the second radiographic image is performed.

Hereinafter, the image of the grid 23 in the first radiographic image is referred to as a "first grid image" and the image of the grid 23 in the second radiographic image is referred to as a "second grid image".

In Step S200 of FIG. 7, the control unit 80 of the console 18 acquires the first radiographic image data and the second radiographic image data. In a case in which the first radiographic image data and the second radiographic image data have been stored in the storage unit 86, the control unit 80 reads and acquires the first radiographic image data and the second radiographic image data from the storage unit 86. In a case in which the first radiographic image data and the second radiographic image data have not been stored in the storage unit 86, the control unit 80 acquires the first radiographic image data from the first radiation detector 20A and acquires the second radiographic image data from the second radiation detector 20B.

Then, in Step S202, the control unit 80 detects the first grid image from the first radiographic image. A method for detecting the first grid image from the first radiographic image in the control unit 80 is not particularly limited. For example, the control unit 80 may generate the grid image, using the frequency components of the grid extracted by passing the radiographic image through a band-pass filter corresponding to the frequency components of the grid. In this embodiment, the "frequency" means a spatial frequency.

Then, in Step S204, the control unit 80 detects the second grid image from the second radiographic image, as in Step S202.

Figure 8:
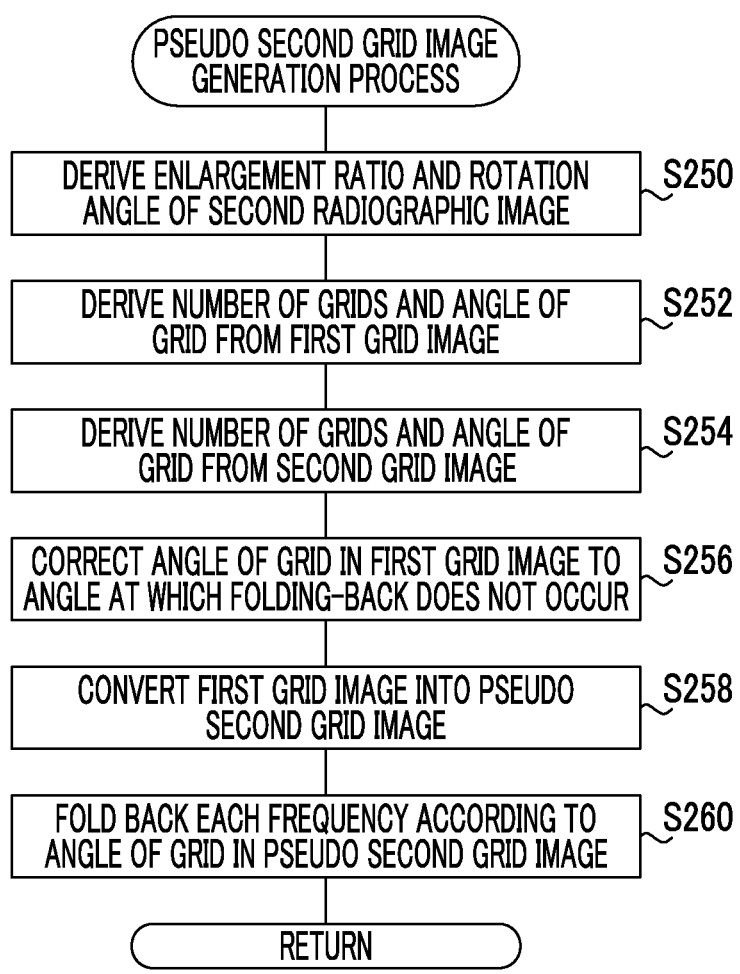
FIG. 8 is a flowchart illustrating an example of the flow of a pseudo second grid image generation process in the image generation process according to this embodiment.

Then, in Step S206, the control unit 80 performs a pseudo second grid image generation process illustrated in FIG. 8 to generate a pseudo second grid image from the first grid image. The "pseudo second grid image" is a pseudo image of the image of the grid 23 included in the second radiographic image. In this embodiment, the pseudo second grid image is not a grid image that is directly detected from the second radiographic image, but is an image generated from the first grid image.

In Step S250 of FIG. 8, the control unit 80 derives the enlargement ratio and rotation angle of the second radiographic image with respect to the first radiographic image. In this embodiment, the enlargement ratio and the rotation angle are derived. However, the invention is not limited to this embodiment. For example, the enlargement ratio, the rotation angle, and the deviation of a center position which is the center of rotation may be derived.

As described above, the second radiation detector 20B is provided so as to be stacked on the side of the first radiation detector 20A from which the radiation R is transmitted and emitted. Therefore, the distance from the radiation source 14 to the first radiation detector 20A is different from the distance from the radiation source 14 to the second radiation detector 20B and the second radiographic image (the image of the subject W) captured by the second radiation detector 20B is an enlarged image of the first radiographic image (the image of the subject W) captured by the first radiation detector 20A. Therefore, in this step, the enlargement ratio of the second radiographic image to the first radiographic image is derived.

Figure 9:
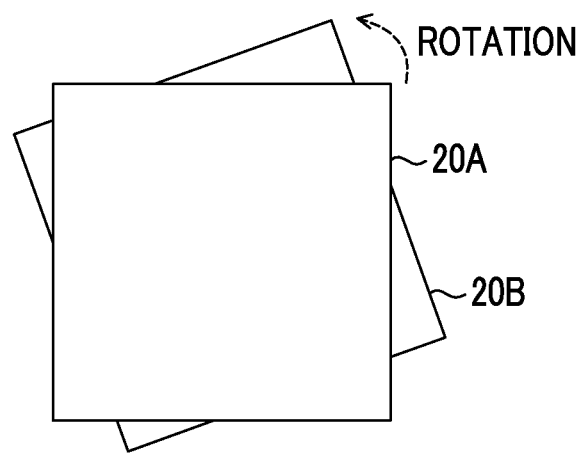
FIG. 9 is a diagram schematically illustrating the positional deviation between the first radiation detector and the second radiation detector.

The first radiation detector 20A and the second radiation detector 20B are provided in the housing 21 in a state in which the positions of each imaging region in the incident direction of the radiation R are aligned with each other, in order to place the image of the subject W at the same position in the first radiographic image and the second radiographic image. However, in some cases, the positional deviation between the first radiation detector 20A and the second radiation detector 20B occurs due to, for example, an error in the attachment of the first radiation detector 20A and the second radiation detector 20B to the housing 21. For example, FIG. 9 illustrates an example of the attachment state of the first radiation detector 20A and the second radiation detector 20B as viewed from the incident side of the radiation R. In the example illustrated in FIG. 9, the second radiation detector 20B is attached to the first radiation detector 20A in a state in which it rotates in the counter clockwise direction and deviates from the first radiation detector 20A in a plan view. In this case, the image of the subject W in the second radiographic image rotates in the clockwise direction with respect to the image of the subject W in the first radiographic image. In other words, the second radiographic image rotates in the clockwise direction with respect to the first radiographic image. Therefore, in Step S250, the rotation angle of the second radiographic image with respect to the first radiographic image, that is, the relative angle between the first radiographic image and the second radiographic image is derived as the amount of deviation between the first radiation detector 20A and the second radiation detector 20B in a direction intersecting the stacking direction.

A method for deriving the enlargement ratio and rotation angle of the second radiographic image with respect to the first radiographic image is not particularly limited.

For example, the enlargement ratio and rotation angle of the second radiographic image with respect to the first radiographic image may be derived from the difference between the positions and sizes of the images of a marker in the first radiographic image and the second radiographic image captured by the radiography apparatus 16 in a state in which the marker is put in advance. For example, the enlargement ratio and rotation angle of the second radiographic image with respect to the first radiographic image may be derived on the basis of the image of the same characteristic structure of the subject W in the first radiographic image and the second radiographic image obtained by capturing the image of the subject W.

Figure 10:
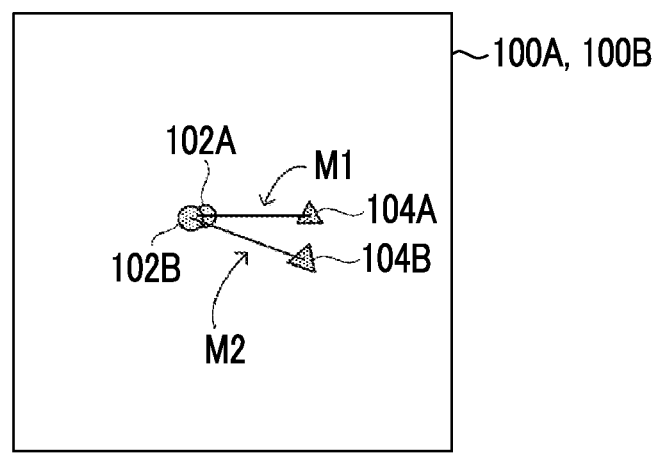
FIG. 10 is a diagram schematically illustrating a state in which the first radiographic image and the second radiographic image captured by the first radiation detector and the second radiation detector that are provided as illustrated in FIG. 9 are superimposed.

An example in which the enlargement ratio and rotation angle of the second radiographic image with respect to the first radiographic image are derived will be described with reference to FIG. 10. FIG. 10 illustrates a state in which a first radiographic image 100A and a second radiographic image 100B captured by the first radiation detector 20A and the second radiation detector 20B that deviate from each other as illustrated in FIG. 9 are superimposed.

FIG. 10 illustrates a state in which two characteristic structures of the subject W are included as a subject image 102A and a subject image 104A in the first radiographic image 100A and are included as a subject image 102B and a subject image 104B in the second radiographic image 100B. Here, the subject image 102A and the subject image 102B are the images of the same structure and the subject image 104A and the subject image 104B are the images of the same structure.

In this case, the magnification ratio of the length of a straight line M2 connecting the subject image 102B and the subject image 104B to the length of a straight line M1 connecting the subject image 102A and the subject image 104A is derived to obtain the enlargement ratio. In addition, the angle of the straight line M2 with respect to the straight line M1 is derived to obtain the rotation angle.

Then, in Step S252, the control unit 80 derives the number of stripes (hereinafter, referred to as "the number of grids") caused by the grid 23 and the angle (hereinafter, referred to as "the angle of the grid") of the stripe caused by the grid 23 with respect to the arrangement direction of the pixels in the radiographic image from the first grid image. In some cases, similarly to the attachment deviation between the first radiation detector 20A and the second radiation detector 20B, the positional deviation between the grid 23 and the first and second radiation detectors 20A and 20B in the arrangement direction of the pixels 32 occurs due to, for example, an error in attachment to the housing 21. In this case, the arrangement direction of the grid 23 is inclined with respect to the arrangement direction of the pixels 32 in the first radiation detector 20A and the second radiation detector 20B. Therefore, the first grid image and the second grid image are included as images with oblique stripes in the first radiographic image 100A and the second radiographic image 100B, respectively.

In this step, for example, the control unit 80 performs frequency analysis for the first grid image to detect the number of stripes in the stripe pattern of the first grid image as the number of grids and performs image analysis for the first grid image to derive the angle of the stripes with respect to the arrangement direction of the pixels 32 as the angle of the grid.

Then, in Step S254, the number of grids and the angle of the grid are derived from the second grid image, as in Step S252.

In general, radiographic image data includes a high-frequency component that is equal to or greater than a Nyquist frequency. The Nyquist frequency $f_N$ [cycles/cm] of the radiation detector in which a pixel pitch is $\Delta$ [cm] is represented by Expression (1).

$$f_N = 1/(2 \times \Delta) \quad (1)$$

For example, when the pixel pitch $\Delta$ is 150 [μm], the Nyquist frequency $f_N$ is 33.33 [cycles/cm].

A high frequency that is equal to or greater than the Nyquist frequency is folded back to the low frequency side with respect to the Nyquist frequency and the folded-back frequency is recorded as an image. Folding at the high frequency that is equal to or greater than the Nyquist frequency is disclosed in, for example, JP5436483B. Specifically, for example, as illustrated in FIG. 11, a frequency $f_G$ and a frequency $2f_G$ are reflected at the Nyquist frequency $f_N$ and a frequency $f=0$ and become a frequency $f_{Gr}$ and a frequency $2f_{Gr}$, respectively.

Figure 11:
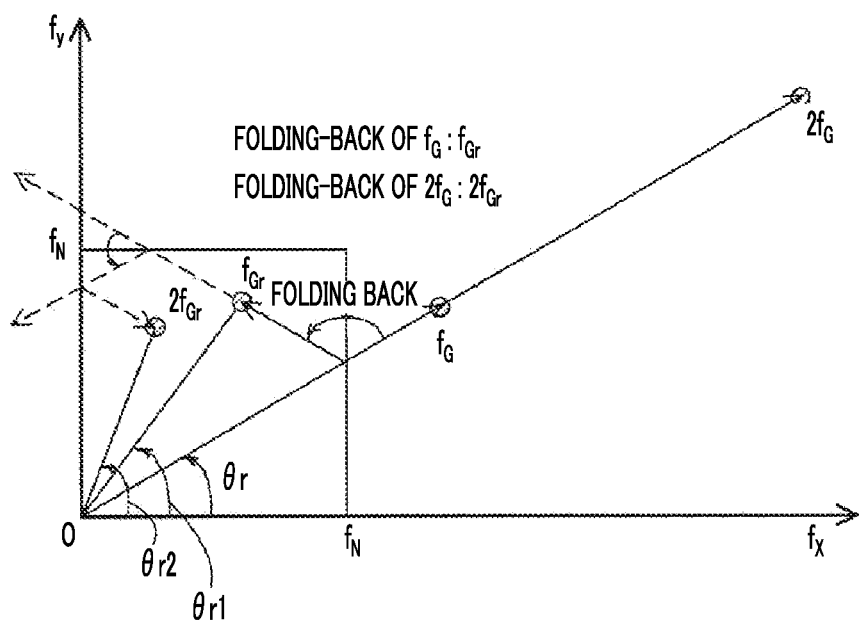
FIG. 11 is a diagram schematically illustrating the folding-back of frequencies at a Nyquist frequency.

For example, in a case in which FIG. 11 is a diagram schematically illustrating the frequency $f_G$ and the frequency $2f_G$ in the first grid image of the first radiographic image 100A, a relative angle θr between the actual grid 23 and the first radiation detector 20A is a relative angle θr1 for the frequency $f_G$ and is a relative angle θr2 for the frequency $2f_G$.

In this embodiment, the control unit 80 performs the following process in order to generate the pseudo second grid image from the first grid image, considering folding back at the Nyquist frequency.

Then, in Step S256, for the frequency F and the harmonics (2F, 3F, . . . ) of the frequency F, the control unit 80 corrects the angle of the grid in the first grid image derived in Step S252 to an angle at which folding back at the Nyquist frequency does not occur. For example, in the example illustrated in FIG. 11, the control unit 80 corrects the relative angle θr1 and the relative angle θr2 to the relative angle θr.

Then, in Step S258, the control unit 80 converts the first grid image into the pseudo second grid image. In this embodiment, in a case in which the number of grids derived in Step S252 is b and the enlargement ratio derived in Step S252 is a %, the first grid image is converted into the number of grids in the pseudo second grid image by Expression (2).

$$\text{The number of grids} = b/(1+a/100) \quad (2)$$

The rotation angle derived in Step S250 is added to the angle of the grid in the first grid image corrected in Step S256 and is converted into the angle of the grid in the pseudo second grid image in which folding back at the Nyquist frequency does not occur.

Then, in Step S260, the control unit 80 estimates how many times each frequency (F, 2F, 3F, . . . ) is folded back at the Nyquist frequency and folds back each frequency at the Nyquist frequency on the basis of the angle of the grid in the pseudo second grid image obtained in Step S258. In this way, the angle of the grid in the pseudo second grid image for each frequency is derived.

When the control unit 80 generates the pseudo second grid image, using the derived angle of the grid and the derived number of grids, the pseudo second grid image generation process ends and the process proceeds to Step S208 of the image generation process illustrated in FIG. 7.

In Step S208, the control unit 80 determines whether the difference between the number of grids in the second grid image derived in Step S254 of the pseudo second grid image generation process in Step S206 and the number of grids in the pseudo second grid image (hereinafter, referred to as a "difference between the numbers of grids") is in a predetermined range. In a case in which the difference between the numbers of grids is not in the predetermined range, the determination result is "No" and the process proceeds to Step S212. On the other hand, in a case in which the difference between the numbers of grids is in the predetermined range, the determination result is "Yes" and the process proceeds to Step S210.

In Step S210, the control unit 80 determines whether the difference between the angle of the grid in the second grid image derived in Step S254 of the pseudo second grid image generation process in Step S206 and the angle of the grid in the pseudo second grid image (hereinafter, referred to as a "difference between the angles") is in a predetermined range. In a case in which the difference between the angles is in the predetermined range, the determination result is "Yes" and the process proceeds to Step S212.

In Step S212, the control unit 80 removes the first grid image from the first radiographic image 100A. Then, in Step S214, the control unit 80 removes the pseudo second grid image generated in Step S206 from the second radiographic image 100B and proceeds to Step S220. In addition, a method for removing the image of the grid 23 of the radiographic image, for example, a method for removing the pseudo second grid image from the second radiographic image 100B is not particularly limited. For example, a reverse pattern of the image of the grid 23 may be superimposed on the radiographic image to remove the image of the grid 23 from the radiographic image.

As such, in the image generation process according to this embodiment, in a case in which there is a large difference in information about the grid between the second grid image detected from the second radiographic image 100B and the pseudo second grid image, the second grid image is unlikely to be an appropriate image. Therefore, the pseudo second grid image is removed to remove an image including the grid 23 from the second radiographic image 100B.

As the predetermined range of the difference between the numbers of grids and the predetermined range of the difference between the angles, predetermined values may be used, considering, for example, errors in the attachment of the first radiation detector 20A and the second radiation detector 20B to the housing 21.

In contrast, in a case in which the difference between the angles is in the predetermined range, the determination result is "Yes" and the process proceeds to Step S216.

In Step S216, the control unit 80 removes the first grid image from the first radiographic image 100A. Then, in Step S218, the control unit 80 removes the second grid image detected in Step S204 from the second radiographic image 100B and proceeds to Step S220.

Then, in Step S220, the control unit 80 generates image data indicating an energy subtraction image, using the first radiographic image data and the second radiographic image data from which the image of the grid 23 has been removed by the above-mentioned process. Hereinafter, the energy subtraction image is referred to as an "ES image" and the image data indicating the energy subtraction image is referred to as "ES image data".

In this embodiment, the control unit 80 subtracts image data obtained by multiplying the first radiographic image data by a predetermined coefficient from image data obtained by multiplying the second radiographic image data by a predetermined coefficient for each corresponding pixel. The control unit 80 generates ES image data indicating an ES image in which soft tissues have been removed and bone tissues have been highlighted, using the subtraction. A method for determining the corresponding pixels of the first radiographic image data and the second radiographic image data is not particularly limited. For example, as in the method for deriving the enlargement ratio and rotation angle of the second radiographic image with respect to the first radiographic image in Step S250 of the pseudo second grid image generation process, the amount of positional deviation may be calculated from the difference between the positions of a characteristic structure of the subject W or a marker in the first radiographic image data and the second radiographic image data and the corresponding pixels of the first radiographic image data and the second radiographic image data may be determined on the basis of the calculated amount of positional deviation.

Then, in Step S222, the control unit 80 determines a bone tissue region (hereinafter, referred to as a "bone region") in the ES image that is indicated by the ES image data generated in Step S220. In this embodiment, for example, the control unit 80 estimates the approximate range of the bone region on the basis of the imaging part included in the imaging menu. Then, the control unit 80 detects pixels that are disposed in the vicinity of the pixels, of which the differential values are equal to or greater than a predetermined value, as the pixels forming the edge (end) of the bone region in the estimated range to determine the bone region.

Figure 12:
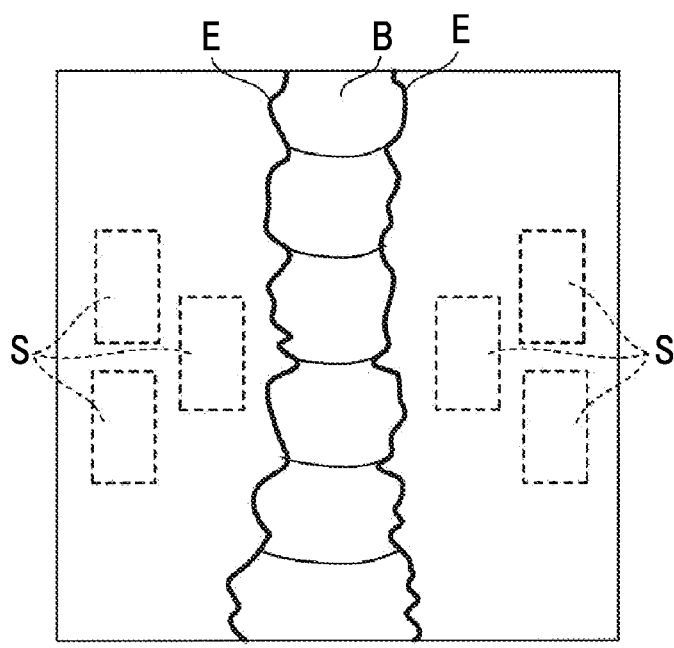
FIG. 12 is a front view schematically illustrating a bone tissue region and a soft tissue region according to this embodiment.

For example, as illustrated in FIG. 12, in Step S222, the control unit 80 detects the edge E of a bone region B and determines a region in the edge E as the bone region B. For example, FIG. 12 illustrates an ES image in a case in which the image of a backbone part of the upper half of the body of the subject W is captured.

A method for determining the bone region B is not limited to the above-mentioned example. For example, the control unit 80 displays the ES image that is indicated by the ES image data generated in Step S220 on the display unit 88. The user designates the edge E of the bone region B in the ES image displayed on the display unit 88 through the operation unit 90. Then, the control unit 80 may determine a region in the edge E designated by the user as the bone region B.

The control unit 80 may display an image in which the ES image and the edge E detected in Step S222 overlap each other on the display unit 88. In this case, in a case in which it is necessary to correct the edge E displayed on the display unit 88, the user corrects the position of the edge E through the operation unit 90. Then, the control unit 80 may determine a region in the edge E corrected by the user as the bone region B.

Then, in Step S224, the control unit 80 determines a soft tissue region (hereinafter, referred to as a "soft region") in the ES image that is indicated by the ES image data generated in Step S220. In this embodiment, for example, the control unit 80 determines a region, which is other than the bone region B and has a predetermined area including pixels that are separated from the edge E by a distance corresponding to a predetermined number of pixels in a predetermined direction, as the soft region. For example, as illustrated in FIG. 12, in Step S224, the control unit 80 determines a plurality of (in the example illustrated in FIG. 12, six) soft regions S.

The predetermined direction and the predetermined number of pixels may be predetermined by, for example, experiments using the actual radiography apparatus 16 according to the imaging part. The predetermined area may be predetermined or may be designated by the user. In addition, for example, the control unit 80 may determine, as the soft region S, the pixels with pixel values in a predetermined range having the minimum pixel value (a pixel value corresponding to a position where the body thickness of the subject W is the maximum except the bone region B) as the lower limit in the ES image data. In addition, it goes without saying that the number of soft regions S determined in Step S224 is not limited to that illustrated in FIG. 12.

Then, in Step S226, the control unit 80 corrects the ES image data generated in Step S220 such that a variation in the ES image in each imaging operation is within an allowable range. In this embodiment, for example, the control unit 80 performs a correction process of removing image blur in the entire frequency band of the ES image data. The image data corrected in Step S226 is used to calculate bone density in a process from Step S228 to Step S232 which will be described below. Therefore, hereinafter, the corrected image data is referred to as "dual-energy X-ray absorptiometry (DXA) image data".

Then, in Step S228, the control unit 80 calculates an average value A1 of the pixel values of the bone region B in the DXA image data. Then, in Step S230, the control unit 80 calculates an average value A2 of the pixel values of all of the soft regions S in the DXA image data. Here, in this embodiment, for example, the control unit 80 performs weighting such that the soft region S which is further away from the edge E has a smaller pixel value and calculates the average value A2. Before the average values A1 and A2 are calculated in Step S228 and Step S230, respectively, abnormal values of the pixel values of the bone region B and the pixel values of the soft region S may be removed by, for example, a median filter.

Then, in Step S232, the control unit 80 calculates the bone density of the imaging part of the subject W. In this embodiment, for example, the control unit 80 calculates the difference between the average value A1 calculated in Step S228 and the average value A2 calculated in Step S230. In addition, the control unit 80 multiplies the calculated difference by a conversion coefficient for converting the pixel value into bone mass [g] to calculate the bone mass. Then, the control unit 80 divides the calculated bone mass by the area [cm$^2$] of the bone region B to calculate bone density [g/cm$^2$]. The conversion coefficient may be predetermined by, for example, experiments using the actual radiography apparatus 16 according to the imaging part.

Then, in Step S234, the control unit 80 stores the ES image data generated in Step S220 and the bone density calculated in Step S232 in the storage unit 86 so as to be associated with information for identifying the subject W. In addition, for example, the control unit 80 may store the ES image data generated in Step S220, the bone density calculated in Step S232, the first radiographic image data, and the second radiographic image data in the storage unit 86 so as to be associated with the information for identifying the subject W.

Then, in Step S236, the control unit 80 displays the ES image indicated by the ES image data generated in Step S220 and the bone density calculated in Step S232 on the display unit 88 and then ends the image generation process.

As described above, the radiography system 10 according to this embodiment comprises: the radiography apparatus 16 comprising the first radiation detector 20A in which a plurality of pixels 32, each of which includes the sensor unit 32A that generates a larger amount of charge as it is irradiated with a larger amount of radiation R, are two-dimensionally arranged and the second radiation detector 20B which is provided so as to be stacked on the side of the first radiation detector 20A from which the radiation R is transmitted and emitted and in which a plurality of pixels 32, each of which includes the sensor unit 32A that generates a larger amount of charge as it is irradiated with a larger amount of radiation R, are two-dimensionally arranged; and the console 18 including the control unit 80. The control unit 80 of the console 18 acquires the first radiographic image 100A acquired by the first radiation detector 20A and the second radiographic image 100B acquired by the second radiation detector 20B, using the grid 23 that removes scattered radiation included in the radiation R which has been transmitted through the subject W. In addition, the control unit 80 detects and removes the first grid image, which is the image of the grid 23, from the acquired first radiographic image 100A and removes the image of the grid 23 from the second radiographic image 100B, using the first grid image.

In the radiography apparatus 16 according to this embodiment, the amount of radiation that reaches the second radiation detector 20B is less than the amount of radiation that reaches the first radiation detector 20A. Therefore, in some cases, the second grid image that is detected from the second radiographic image 100B captured by the second radiation detector 20B is not appropriate as the image of the grid 23. In this case, the control unit 80 of the console 18 generates the pseudo second grid image which is a pseudo image of the image of the grid 23 included in the second radiographic image 100B, using the first grid image that is detected from the first radiographic image 100A captured by the first radiation detector 20A. Then, the control unit 80 performs image processing for removing the second grid image from the second radiographic image 100B.

Therefore, according to the radiography system 10 of this embodiment, even when the amount of radiation R emitted to the second radiation detector 20B is less than the amount of radiation R emitted to the first radiation detector 20A, it is possible to perform appropriate image processing for the acquired radiographic image.

In the image generation process according to this embodiment, the pseudo second grid image is removed from the second radiographic image 100B in a case in which there is a large difference in information about the grid between the second grid image detected from the second radiographic image 100B and the pseudo second grid image. However, the invention is not limited thereto. For example, in a case in which there is a large difference between the number of grids or the angle of the grid in the second grid image and an assumed value obtained by experiments, a process that removes the pseudo second grid image from the second radiographic image 100B, without determining the difference between the second grid image and the pseudo second grid image, may be performed. In addition, even in a case in which it is difficult to detect the second grid image from the second radiographic image 100B, the process that removes the pseudo second grid image from the second radiographic image 100B may be performed.

In this embodiment, the case in which the number of grids and the angle of the grid are used as the difference between the second grid image and the second radiographic image has been described. However, the invention is not limited thereto. For example, one of the number of grids and the angle of the grid may be used as the difference. In addition, the difference may be, for example, the position of the stripes with respect to the second radiographic image 100B.

In this embodiment, the case in which the enlargement ratio and rotation angle of the second radiographic image 100B with respect to the first radiographic image 100A are derived has been described. However, the reduction ratio and rotation angle of the first radiographic image 100A with respect to the second radiographic image 100B may be derived.

The control unit 80 according to this embodiment may store the first radiographic image 100A and the second radiographic image 100B from which the image of the grid 23 has been removed in the storage unit 86. In this case, the second radiographic image 100B may be stored so as to be associated with information indicating which of the second grid image and the pseudo second grid image has been removed.

In this embodiment, the case in which the second radiographic image 100B from which the second grid image has been removed and the second radiographic image 100B from which the pseudo second grid image has been removed are generated has been described. However, the invention is not limited thereto. The two second radiographic images 100B may be generated. In this case, for example, both the second radiographic image 100B from which the second grid image has been removed and the second radiographic image 100B from which the pseudo second grid image has been removed may be presented to the user such that the user can select one of the two second radiographic images 100B to be used to derive bone density.

In this embodiment, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B.

In this embodiment, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In this embodiment, the case in which the radiography apparatus 16 is controlled by two control units (control units 58A and 58B) has been described. However, the invention is not limited thereto. For example, the radiography apparatus 16 may be controlled by one control unit. In addition, in this embodiment, the case in which the control unit 80 of the console 18 functions as an example of the acquisition unit and the removal unit according to the invention. However, the invention is not limited thereto. For example, one of the control unit 58A and the control unit 58B or other apparatuses, such as reading apparatuses, different from the radiography apparatus 16 and the console 18 may have the functions of at least one of the acquisition unit or the removal unit.

In this embodiment, the case in which bone density is derived using the first radiographic image 100A and the second radiographic image 100B has been described. However, the invention is not limited thereto. For example, bone mineral content or both bone density and bone mineral content may be derived using the first radiographic image 100A and the second radiographic image 100B.

In this embodiment, the aspect in which the overall imaging processing program is stored (installed) in the ROM 80B in advance has been described. However, the invention is not limited thereto. The overall imaging processing program may be recorded in a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through a network.

What is claimed is:

1. A radiography system comprising:
    a radiography apparatus comprising
        a first radiation detector in which a plurality of pixels, each of which includes a conversion element that generates a larger amount of charge as it is irradiated with a larger amount of radiation, are two-dimensionally arranged,
        a second radiation detector which is stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, and
        a grid that is configured to remove scattered radiation included in the radiation transmitted through a subject; and
    an acquisition unit that is configured to acquire, using the grid, a first radiographic image captured by the first radiation detector and a second radiographic image captured by the second radiation detector; and
    a removal unit that is configured to detect and remove a first grid image, which is an image of the grid, from the first radiographic image acquired by the acquisition unit, and to remove the image of the grid from the second radiographic image acquired by the acquisition unit, using the first grid image.

2. The radiography system according to claim 1,
    wherein the removal unit is configured to generate, using the first grid image, a pseudo second grid image, which is a pseudo image of the image of the grid included in the second radiographic image, from the first grid image, and to remove the generated pseudo second grid image as the image of the grid from the second radiographic image.

3. The radiography system according to claim 2,
    wherein the removal unit is configured to generate the pseudo second grid image from the first grid image, using an amount of deviation between the first radiation detector and the second radiation detector in a direction intersecting a stacking direction of the first radiation detector and the second radiation detector, and an enlargement ratio of the second radiographic image to the first radiographic image.

4. The radiography system according to claim 3,
    wherein the removal unit is configured to derive a rotation angle of the second radiation detector with respect to the first radiation detector as the amount of deviation in the direction intersecting the stacking direction, and
    the removal unit is configured to generate the pseudo second grid image from the first grid image, using the rotation angle, the enlargement ratio, and folding back at a Nyquist frequency that is defined by a gap between adjacent pixels of the plurality of pixels of the first radiation detector.

5. The radiography system according to claim 2,
    wherein, in a case in which a second grid image, which is an image of the grid, is capable of being detected from the second radiographic image and a difference in information of the grid between the second grid image and the pseudo second grid image is in a predetermined range, the removal unit is configured to remove the second grid image as the image of the grid from the second radiographic image, without using the first grid image.

6. The radiography system according to claim 5, wherein the difference is at least one of a difference between a number of grids in the second grid image and a number of grids in the pseudo second grid image, or a relative angle of the grid between the second grid image and the pseudo second grid image.

7. The radiography system according to claim 1, wherein each of the first radiation detector and the second radiation detector comprises a light emitting layer that emits light as a result of being irradiated with radiation, the plurality of pixels of each of the first radiation detector and the second radiation detector generate and accumulate the charge as a result of receiving the light, and the light emitting layer of the first radiation detector and the light emitting layer of the second radiation detector have different compositions.

8. The radiography system according to claim 7, wherein the light emitting layer of the first radiation detector includes CsI, and the light emitting layer of the second radiation detector includes GOS.

9. The radiography system according to claim 1, further comprising:
a derivation unit that is configured to derive at least one of bone mineral content or bone density, using the first radiographic image and the second radiographic image from which the image of the grid has been removed by the removal unit.

10. The radiography system according to claim 1, wherein the radiography apparatus further comprises a radiation limitation member that is provided between the first radiation detector and the second radiation detector and absorbs a larger amount of specific component than other components in energy forming the radiation.

11. The radiography system according to claim 1, wherein the first and second radiation detectors are stacked in a radiation irradiation direction such that entire imaging planes of the first and second radiation detectors substantially overlap with each other.

12. An image processing method using a radiography apparatus comprising a first radiation detector in which a plurality of pixels, each of which includes a conversion element that generates a larger amount of charge as it is irradiated with a larger amount of radiation, are two-dimensionally arranged, a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, and a grid that is configured to remove scattered radiation included in the radiation transmitted through a subject, the method comprising:
acquiring a first radiographic image captured by a first radiation detector and a second radiographic image captured by the second radiation detector, using the grid;
detecting and removing a first grid image, which is an image of the grid, from the first radiographic image; and
removing a second grid image, which is the image of the grid, from the second radiographic image, using the first grid image.

13. The image processing method according to claim 12, wherein the first and second radiation detectors are stacked in a radiation irradiation direction such that entire imaging planes of the first and second radiation detectors substantially overlap with each other.

14. A non-transitory storage medium storing an image processing program that causes a computer to perform an image processing using a radiography apparatus comprising a first radiation detector in which a plurality of pixels, each of which includes a conversion element that generates a larger amount of charge as it is irradiated with a larger amount of radiation, are two-dimensionally arranged, a second radiation detector which is provided so as to be stacked on a side of the first radiation detector from which the radiation is transmitted and emitted and in which a plurality of pixels, each of which includes a conversion element that generates a larger amount of charge as it is irradiated with a larger amount of radiation, are two-dimensionally arranged, and a grid that is configured to remove scattered radiation included in the radiation transmitted through a subject, the image processing comprising:
acquiring a first radiographic image captured by a first radiation detector and a second radiographic image captured by the second radiation detector, using the grid;
detecting and removing a first grid image, which is an image of the grid, from the first radiographic image; and
removing a second grid image which is the image of the grid from the second radiographic image, using the first grid image.

15. The non-transitory storage medium according to claim 14, wherein the first and second radiation detectors are stacked in a radiation irradiation direction such that entire imaging planes of the first and second radiation detectors substantially overlap with each other.

* * * * *